United States Patent [19]

Mase et al.

[11] Patent Number: 4,505,803
[45] Date of Patent: * Mar. 19, 1985

[54] OXYGEN CONCENTRATION DETECTOR

[75] Inventors: Syunzo Mase, Ama; Shigeo Soejima, Nagoya, both of Japan

[73] Assignee: NGK Insulators, Ltd., Japan

[*] Notice: The portion of the term of this patent subsequent to Oct. 4, 2000 has been disclaimed.

[21] Appl. No.: 383,218

[22] Filed: May 28, 1982

[30] Foreign Application Priority Data

Jun. 4, 1981 [JP] Japan .................................. 56-84971

[51] Int. Cl.³ ............................................ G01N 27/46
[52] U.S. Cl. .................................. 204/425; 204/412; 204/426; 204/427; 204/429; 219/505; 219/553; 422/98
[58] Field of Search ..................... 204/1 S, 421–429; 422/98; 219/505, 553

[56] References Cited

U.S. PATENT DOCUMENTS

| | | | |
|---|---|---|---|
| 3,751,968 | 8/1973 | Loh et al. | 422/98 |
| 3,924,098 | 12/1975 | Dunn | 219/553 |
| 4,101,454 | 7/1978 | Kulwicki et al. | 219/553 |
| 4,224,280 | 9/1980 | Takahama et al. | 422/98 |
| 4,293,838 | 10/1981 | Wahlers et al. | 219/553 |
| 4,298,573 | 11/1981 | Fujushiro | 204/425 |
| 4,321,577 | 3/1982 | Carlson | 422/98 |
| 4,338,281 | 7/1982 | Treitinger et al. | 422/98 |
| 4,407,704 | 10/1983 | Mase et al. | 204/425 |

FOREIGN PATENT DOCUMENTS

| | | | |
|---|---|---|---|
| 0030164 | 6/1981 | European Pat. Off. | 204/427 |
| 79246 | 6/1981 | Japan | 204/428 |

*Primary Examiner*—T. Tung
*Attorney, Agent, or Firm*—Parkhurst & Oliff

[57] ABSTRACT

The disclosed oxygen concentration detector includes at least one resistive body and at least one semiconductor whose resistance varies with oxygen partial pressure, and an alternating current of a specific frequency is applied to the resistive body so as to raise the temperature thereof, which resistive body is adapted to heat the semiconductor.

10 Claims, 16 Drawing Figures

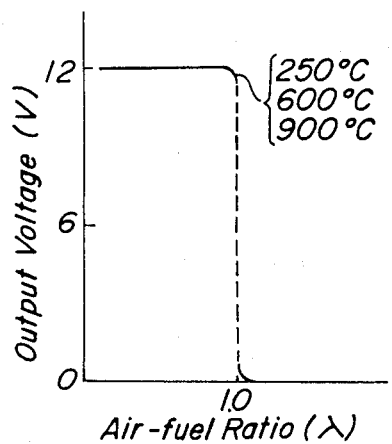
FIG_13
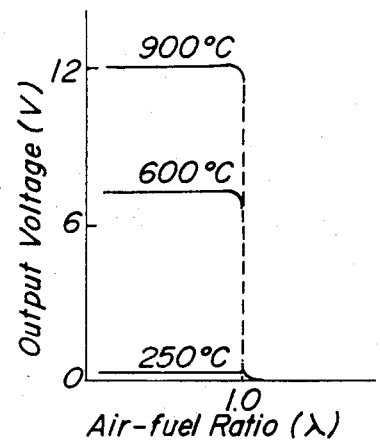
FIG_14
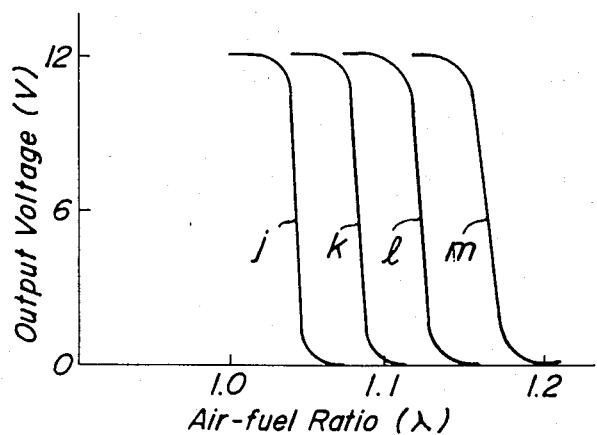
FIG_15

OXYGEN CONCENTRATION DETECTOR

BACKGROUND OF THE INVENTION

1. Field of the Invention

This invention relates to an oxygen concentration detector for detecting the oxygen concentration of a gas, which detector is particularly suitable for detecting the oxygen concentration of a gas at a low temperature.

2. Description of the Prior Art

To detect the oxygen concentration in exhaust gas from internal combustion engine, oxygen concentration detectors having metal oxide semiconductors, such as titania ($TiO_2$) or zinc oxide ($ZnO$), whose electric resistance varies with the oxygen partial pressure in the ambient gas have been known.

The oxygen concentration detectors of the prior art using the above-mentioned metal oxide semiconductors have shortcomings in that the resistance value thereof at low temperatures is very high for both the deficient oxygen concentration and the excess oxygen concentration, and such very high resistance value renders the oxygen concentration detector susceptible to adverse effects of noises, and in that a large time lag exists in variation of the resistance value in response to a change in the oxygen concentration of the exhaust gas. Due to such shortcomings, the lowest temperature limit for practical use of the above-mentioned conventional oxygen concentration detectors has been about 300° C. On the other hand, the temperature of the exhaust gas from internal combustion engines is below the above-mentioned lowest temperature limit at the start or during slow running of the engines, so that the conventional oxygen concentration detectors with metal oxide semiconductors have not been used to their full capability.

To solve such shortcomings, an oxygen sensor with a heater disposed in juxtaposition with a metal oxide semiconductor has been proposed. However, the proposed use of the heater has a shortcoming in that, since the temperature of the gas to be measured such as the exhaust gas of internal combustion engines can be very high, the heater material must withstand the high temperature without any deterioration and noble metals such as platinum and rhodium are often used, and due to the low specific resistance of the noble metals and other heat-resistive materials the heater wires must be very thin, so that the structure of the heater becomes complicated and large and the heater wires are susceptible to breakage. Besides, a large power of several tens of watts is necessary to heat the metal oxide semiconductor.

Furthermore, the resistance value of the metal oxide semiconductor varies greatly with temperature, so that temperature correction of the resistance value has been necessary to determine the deficient air (rich burn) or excess air (lean burn).

In view of the fact that the oxygen concentration of the exhaust gas varies noticeably when the air-fuel ratio $\lambda$ thereof is in the proximity of 1.0, the oxygen concentration detectors of the above-mentioned type have been used mostly for controlling the air-fuel ratio $\lambda$ of the exhaust gas of internal combustion engine at 1.0 by utilizing the large change of resistance value of the metal oxide semiconductor in response to the large variation of the oxygen concentration thereat. However, with the conventional oxygen concentration detectors, it has been impossible to provide the rich burn control ($\lambda < 1.0$) for ensuring a high output efficiency or the lean burn control ($\lambda > 1.0$) for ensuring a good fuel efficiency.

SUMMARY OF THE INVENTION

Therefore, an object of the present invention is to obviate the above-mentioned shortcomings of the prior art by providing an improved oxygen concentration detector. The oxygen concentration detector of the invention has excellent accuracy and response at low temperatures, and provides the control of the air-fuel ratio at an arbitrary value with a low power consumption, and yet it is compact in size and highly durable.

To fulfil the object, the oxygen concentration detector according to the present invention comprises at least one semiconductor whose electric resistance varies with oxygen partial pressure of ambient atmosphere thereof; at least one resistive body having a composition including a plurality of portions with a negative temperature coefficient of electric resistance and high-resistance substance layers separating said portions one from the other, and electrodes mounted on said composition, the impedance of said resistive body depending only on distributed constants of said composition for frequencies higher than a certain boundary frequency; and an AC power source adapted to apply an AC current to said resistive body so as to heat the resistive body, said AC current having a frequency higher than said certain boundary frequency, said resistive body being so related to said semiconductor that said semiconductor is heated by said resistive body upon application of said AC current.

In a preferred embodiment of the invention, at least one solid electrolyte is formed by said resistive body, and a direct current is applied to the solid electrolyte so as to control the oxygen partial pressure at the surface or voids of the semiconductor.

In another embodiment of the invention, the impedance of said resistive body is measured by applying an AC current thereto, the frequency of said AC current being such that most of AC polarization is formed in the inside of said resistive body.

An object of the present invention is to provide an oxygen concentration detector for detecting oxygen concentration in gases, comprising: at least one semiconductor whose electric resistance varies with oxygen partial pressure of ambient atmosphere thereof; at least one resistive body having a composition including a number of portions with a negative temperature coefficient of electric resistance and high-resistance substance layers separating said portion one from the other, and electrodes contacting said composition; an AC power source adapted to apply an AC current to said resistive body so as to heat the resistive body, said AC power source being operable at AC frequencies which are not lower than a frequency whose complex impedance characteristics which when graphed in the manner shown in FIG. 7 hereof, correspond to point B of said graphed complex impedance characteristics, said resistive body being so related to said semiconductor that said semiconductor is heated by said resistive body upon application of said AC current; and means for measuring a resistance of the semiconductor.

Another object of the present invention is to provide an oxygen concentration detector for detecting oxygen concentration in gases, comprising: at least one semiconductor whose electric resistance varies with oxygen partial pressure of ambient atmosphere thereof; at least one of resistive body having a composition including a number of portions with a negative temperature coefficient of electric resistance and high-resistance substance layers separating said portions one from the other, and electrodes contacting said composition, at least one of said composition being oxygen ion conductive solid electrolyte which forms an oxygen pump; an AC power source adapted to apply an AC current to said resistive body so as to heat the selected resistive body, said AC power source being operable at AC frequencies which are not lower than a frequency whose complex impedance characteristics which when graphed in the manner shown in FIG. 7 hereof correspond to point B of said graphed complex impedance characteristics, said resistive body being so related to semiconductor that said semiconductor is heated by said resistive body upon application of said AC current; a DC source adapted to apply a DC current to said oxygen pump so as to control oxygen partial pressure around the semiconductor; and means for measuring a resistance of the semiconductor.

The further object of the present invention is to provide the detector, wherein said portions with a negative temperature coefficient of electric resistance are fine grains.

The still further object of the present invention is to provide the detector, wherein said portions with a negative temperature coefficient of electric resistance are thin films.

Another object of the present invention is to provide the detector, wherein an AC current and AC voltage between the electrode have a negative relation, in which one increases, the other decreases.

Another object of the present invention is to provide the detector, wherein the AC current has a frequency at which an impedance of electrostatic capacitance $C_2$ at the highly resistant region layers interposed between the fine particles or thin film is smaller than a resistance $R_2$ at the highly resistant region layers.

Another object of the present invention is to provide the detector further comprising means for detecting the impedance of selected one of said resistive bodies by applying an AC current thereto, said AC current having a frequency which is not lower than a frequency whose complex impedance characteristics, when graphed in the manner shown in FIG. 7 hereof, correspond to point B of said graphed complex impedance characteristics.

Another object of the present invention is to provide the detector further comprising an auxiliary heating means related to one of said resistive body.

Another object of the present invention is to provide the detector, wherein one electrode of said semiconductor is connected to one electrode of said resistive body through a capacitor, said resistive body being heated by said AC current.

BRIEF DESCRIPTION OF THE DRAWINGS

For a better understanding of the invention, reference is made to the accompanying drawings, in which:

FIGS. 13 through 15 are diagrams for explanation of the example of the present invention.

Figure 1:
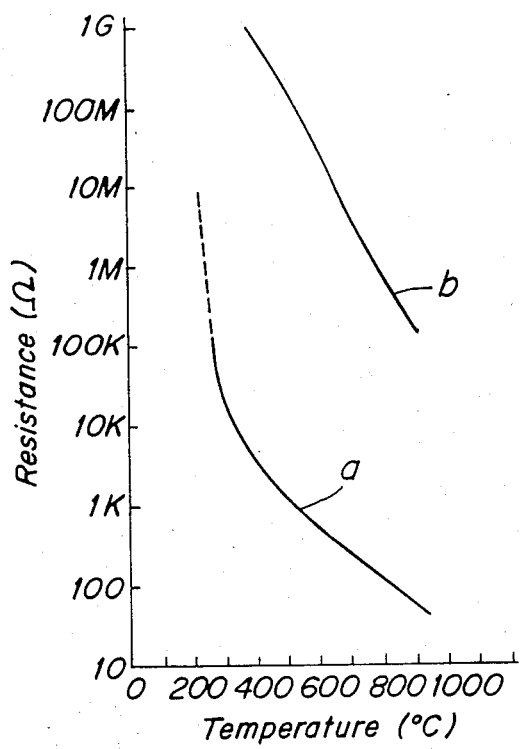
FIG. 1 is a graph showing the relationship between the temperature and the resistance of a metal oxide semiconductor.

Throughout different views of the drawing, 1 is a fine grain, 2 is a high-resistance substance layer, 3 and 4 are electrodes, 5 is a thin film, 6 is a high-resistance substance layer, 7 and 8 are electrodes, 9 is a metal oxide semiconductor, 10 is a resistive body, 11 is a diffusion layer, 12 is an AC power source, 13 is a current-limiting resistor, 14 is a current-detecting resistor, 15 and 16 are DC power sources, 17 is a current-detecting resistor, 18 is a DC voltage detector, 19 is an AC voltage detector, 20 and 21 are electrodes, 23 is a disk-like titania porcelain, 24 and 25 are electrodes, 26 is solid electrolyte, 27 is an alumina case, 28 is a diffusion layer, 29 is an AC power source, 30 is a current-limiting resistor, 31 and 32 are DC power sources, 33 is a current-detecting resistor, 34 is a DC voltage detector, 36 and 37 are electrodes, 38 is a resistive body, 39 is a DC power source, 40 is an inductor, 41 is a resistor, and 42 is a capacitor.

DESCRIPTION OF THE PREFERRED EMBODIMENTS

Referring to FIG. 1, the resistance values of a metal oxide semiconductor placed in an exhaust gas is very high at low temperature, regardless of whether of exhaust gas is of deficient oxygen concentration (as shown by the curve (a) or of excess oxygen concentration (as shown by the curve (b). If such high resistance value of the metal oxide semiconductor is directly used in an oxygen concentration detector, the shortcomings of the prior art as pointed out in the foregoing cannot be solved.

The present invention is to obviate the difficulties relating to the high resistance of the metal oxide semiconductor at low temperatures, by disposing a resistive body by the side of such semiconductor and applying an alternating current of a certain frequency to the resistive body so as to heat the resistive body and indirectly heat the semiconductor.

Figure 2:
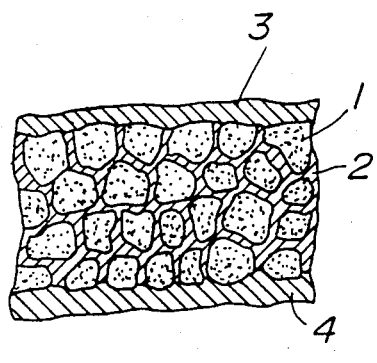
FIGS. 2 and 3 are fractional schematic sectional views of resistive bodies which are used in the oxygen concentration detector of the invention.
Figure 3:
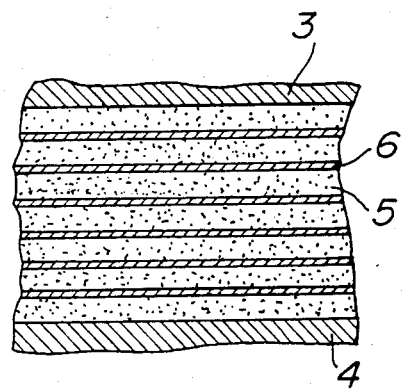

Referring to FIG. 2 showing a practical example of a resistive body to be used in the oxygen concentration detector of the present invention, fine grains 1 have a negative temperature coefficient of electric resistance (to be referred to as NTCR hereinafter) and high-resistance substance layers 2 separating the fine grains 1 one from the other. The fine grains 1 and the high-resistance substance layers 2 form a composition, and electrodes 3 and 4 are mounted on opposite and surfaces of the composition. For instance, the composition of the resistive body is a ceramic material such as ceramics of zirconia ($ZrO_2$) porcelain, titania ($TiO_2$) porcelain, zinc oxide (ZnO), tin oxide ($SnO_2$), or barium titanate ($BaTiO_3$); or a composition formed by binding fine grains of semiconductor such as metallic silicon (Si) with high-resistance glass or silicon oxide. In such composition, the fine grains 1 are formed of fine crystals of $ZrO_2$, $TiO_2$, ZnO, $SnO_2$, $BaTiO_3$, or Si, while the high-resistance substance layers 2 are formed of grain boundaries, glass, or silicon oxide. FIG. 3 shows a difference microscopic structure of the resistive body, wherein material with an NTCR is formed in thin films 5, which thin films 5 correspond to the fine grains 1 of FIG. 2, and high-resistance layers 6 are formed so as to separate the above-mentioned thin films 5 with NTCR one from the other.

Figure 4:
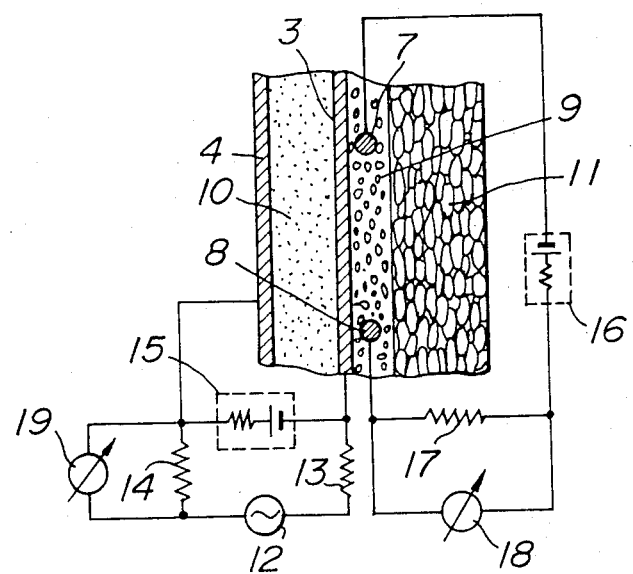
FIG. 4 is a diagrammatic illustration of an embodiment of the oxygen concentration detector according to the present invention.

Referring to FIG. 4 illustrating an embodiment of the present invention, electrodes 7 and 8 are embedded in a porous metal oxide semiconductor 9, which semiconductor 9 is for instance made of titania ($TiO_2$) and has an electric resistance varying with oxygen partial pressure of the ambient atmosphere thereof. A resistive body 10, which is for instance made of zirconia ($ZrO_2$) and has electrodes 3 and 4, is disposed in juxtaposition with the semiconductor 9 while keeping the electrode 3 in contact with one side surface of the semiconductor 9. A porous diffusion layer 11 made of alumina spinel or the like is mounted on the opposite side surface of the semiconductor 9. An AC power source 12 is connected across the electrodes 3 and 4 through a current-limiting resistor 13 and a current-detecting resistor 14. The frequency of the AC power source 12 is such that most of the AC polarization of the current path thereof is caused in the inside of the resistive body 10. A DC power source 15 is connected across the electrodes 4 and 3, so as to cause a direct current to flow from the electrode 4 to the electrode 3 through the resistive body 10. Another DC power source 16 is connected across the electrodes 7 and 8 of the metal oxide semiconductor 9 through a current-detecting resistor 17. A DC voltage detector 18 is connected across the current-detecting resistor 17, so as to monitor the voltage across it. An AC voltage detector 19 is connected across the current-detecting resistor 14 for monitoring the voltage across it, whereby the impedance of the resistive body 10 is detected. Thus, an oxygen concentration detector is assembled. The outer surface of the diffusion layer 11 and the electrode 4 are exposed to the gas to be measured.

Figure 5:
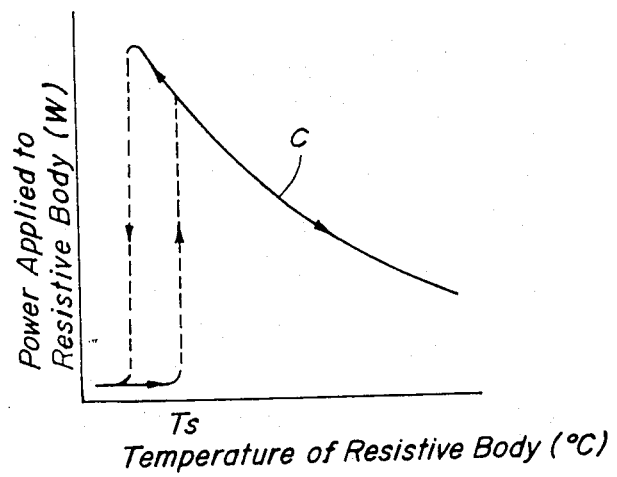
FIG. 5 is a graph showing the relationship between the temperature of the resistive body used in the invention and the electric power applied thereto.

In the oxygen concentration detector of the above-mentioned structure, self-heating of the resistive body 10 is caused upon application of an AC voltage thereto from the AC power source 12, and the heat from the resistive body 10 raises the temperature of the metal oxide semiconductor 9 for initiating the operation of the semiconductor 9 at a high temperature. The current-limiting resistor 13 connected between the resistive body 10 and the heating AC power source 12 protects the resistive body 10 from the risk of a large overcurrent flowing thereto. When the resistive body 10 is hot and heating is not necessary, the electric power applied to the resistive body 10 is suppressed to a low level. The curve C of FIG. 5 shows the relationship between the temperature of the resistive body 10 and the power applied thereto, which curve indicates negative characteristics at high temperatures. It is possible to provide the temperature self-control properties to the resistive body 10 by operating it at the negative characteristics portion of the curve C. Thereby, the width of the temperature change of the metal oxide semiconductor 9 can be kept small for an expected range of the temperature change of the gas to be measured, so that the temperature correction of the resistance value of the metal oxide semiconductor 9 may be dispensed with.

In the present invention, the oxygen concentration at the boundary between the electrode 3 and the metal oxide semiconductor 9 is controlled by the "oxygen pump" action caused by the direct current applied to the resistive body 10, and accordingly, the oxygen concentration at the metal oxide semiconductor 9 is controlled. More particularly, oxygen in the gas being measured diffuses toward the electrode 3 through the porous diffusion layer 11 and the metal oxide semiconductor 9 at a diffusion speed proportional to the oxygen concentration difference across the surface of the diffusion layer 11 exposed to the gas being measured and the surface of the electrode 3 in contact with the metal oxide semiconductor 9. The thus diffusing oxygen ionize at the boundary between the measuring electrode 3 and the resistive body 10 through the following reaction.

The oxygen ions then move through the resistive body 10 until arriving at the electrode 4 where they are reconverted into oxygen gas and emitted therefrom. Accordingly, there is the following relationship between the oxygen concentration Co in the gas being measured and the oxygen concentration Ce at the boundary between the electrode 3 and the resistive body 10, provided that the diffusion resistance of the metal oxide semiconductor 9 can be assumed to be negligible.

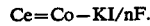

Here, I represents the current density of the direct current flowing through the electrode 3, K is a constant representing the diffusion resistance of the diffusion layer 11 for oxygen gas, n is a charge number in the reaction at the electrode which charge number is 4 in this case, and F is the Faraday constant.

In the oxygen concentration detector using the metal oxide semiconductor 9, the resistance value of the metal oxide semiconductor 9 varies suddenly for slight excess oxygen or slight deficient oxygen in the atmosphere of nearly zero (0) oxygen concentration in the metal oxide semiconductor 9. Accordingly, it is noted that the oxygen concentration Ce at the above-mentioned boundary can be made zero at an arbitrary value of the oxygen concentration Co in the gas being measured, by selecting such values of the constants K and I which render KI/nF=Co. Since the resistance value of the metal oxide semiconductor varies suddenly when the oxygen concentration Ce at the above-mentioned boundary is zero, an arbitrary oxygen concentration in the exhaust gas, which oxygen concentration is different from that at the air-fuel ratio $\lambda=1.0$, can be now detected accurately and easily by regulating the values of K and I.

The impedance of the resistive body 10 is reduced to an extremely small value by the above-mentioned self-heating, so that the voltages across the boundaries between the resistive body 10 and the electrode 3 and between the resistive body 10 and the electrode 4 are low, and the electrodes 3 and 4 are free from chipping even after a long period of operation. Besides, the heat generation in the resistive body 10 has the temperature self-control properties, so that the variation of the oxygen diffusion speed due to the temperature change of diffusion layer 11 can be minimized, and the temperature correction can be easily effected even if necessary.

In the heating of the resistive body according to the present invention, an AC power source with that frequency which causes the AC polarization to occur mainly in the inside of the resistive body is used. The reason for using such AC frequency will be explained now.

Figure 6:
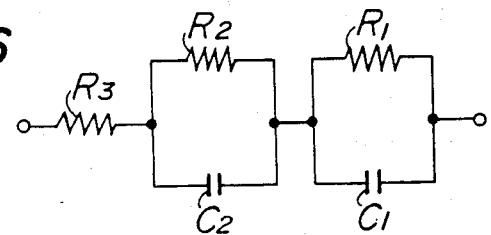
FIG. 6 is an equivalent circuit diagram of the resistive body.
Figure 7:
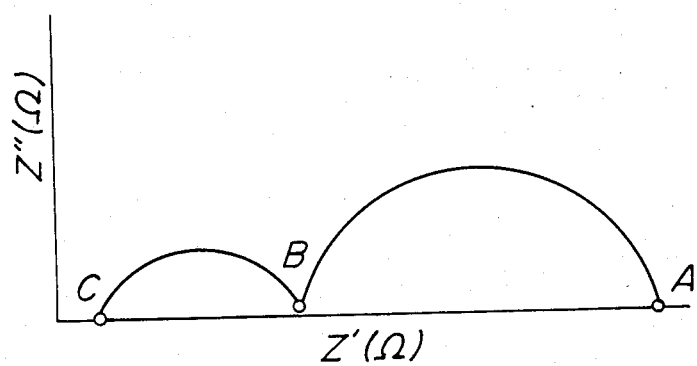
FIG. 7 is a graph showing the impedance characteristics of the resistive body.

FIG. 6 shows an electrical equivalent circuit of the resistive body having electrodes as shown in FIG. 2 or FIG. 3, which resistive body includes the above-mentioned fine grains or thin films with an NTCR and high-resistance substance layers separating the fine grains or thin films one from the other. In the equivalent circuit of FIG. 6, $R_1$ is a polarization resistance component at the boundary between the electrode and the resistive body, $C_1$ is an electrostatic capacitance component due to the polarization at the boundary between the electrode and the resistive body, $R_2$ is a resistance component at the high-resistance substance layer between the NTCR fine grains or thin films, $C_2$ is an electrostatic capacitance component of the high-resistance substance layer, and $R_3$ is a resistance component of the NTCR fine grains or thin film. The frequency characteristics of the complex impedance $Z = Z' - jZ''$ of the resistive body, as represented by the equivalent circuit of FIG. 6, includes two continuous arcuate portions as shown in FIG. 7. In FIG. 7, the resistance value of point A corresponds to the sum of the three resistance components $R_1 + R_2 + R_3$ of FIG. 6, the resistance value of point B corresponds to the sum of the two resistance components $R_2 + R_3$, and the resistance value of point C corresponds to the resistance component $R_3$. The polarization of the resistive body from the point A to the point B on the frequency characteristics curve of FIG. 7 is mainly due to the resistance component $R_1$ and the capacitance component $C_1$, and that from the point B to the point C is mainly due to the resistance components $R_2$, $R_3$ and the capacitance component $C_3$. As regards the variation of the complex impedance characteristics with the frequency variation, the point A represents DC, and as the frequency increases, the complex impedance characteristics varies along the arcuate locus toward the point B and further along the other arcuate locus toward the point C.

The arcuate characteristics from the point A to the point B of FIG. 7 varies considerably depending on the surface conditions of the resistive body, on the manner in which the electrodes are mounted on the resistive body, and on the time length of using the resistive body. Accordingly, if an AC voltage of a frequency in the range between the points A and B is used, it is difficult to apply electric power necessary for the heating in a stable fashion. When the resistive body is designed for use at a high temperature and electrodes of refractory materials such as platinum electrodes are used, or when solid electrolyte is used as the resistive body, the arcuate locus between the points A and B of FIG. 7 generally becomes very large at low temperatures. Accordingly, if the frequency in the range between the points A and B is used in such cases, feeding of electric power becomes difficult unless the voltage is raised in this frequency range between the points A and B, and difficulties accompanying the high voltages such as induction interference from the lead wires and reduced durability of the electrodes are caused. Besides, high voltages are generated at the boundaries between the electrodes and the resistive body, and such high voltages tend to cause chipping of the electrodes and chemical decay of the resistive body surface. With such high voltages, slight difference in the properties between the electrodes tends to cause deviation of the DC components, and the control of the oxygen partial pressure by the direct current will become very inaccurate when oxygen-ion-conductive solid electrolyte is used as the above-mentioned resistive body 10 as shown in FIG. 4.

On the other hand, in the heating of the resistive body according to the present invention, an alternating current of the frequency which generates polarization mainly in the inside of the resistive body, i.e., the frequency higher than that for the point B of FIG. 7, is applied to the resistive body. Thus, even when the alternating current is large enough for heating the resistive body, no chipping of the electrodes and no chemical decay and no breakage of the resistive body are caused. The reason for the elimination of the electrode chipping and the electrolyte decay appears to be in that, when an AC voltage with a frequency higher than that for the point B of FIG. 7 is applied to the resistive body, most of the polarization occurs in the composition of the resistive body represented by the components $R_2$, $C_2$, and $R_3$ collectively designating the distributed constants thereof, and the polarization within the resistive body is uniformly distributed in the direction of the thickness thereof, whereby chemical change or decay due to electric current therethrough hardly occur. Furthermore, at the boundaries between the electrodes and the resistive body represented by the constants $R_1$ and $C_1$ where electrolyte decay normally occurs, polarization hardly occurs at the frequency above that for the point B of FIG. 7, so that such boundaries are protected against the above-mentioned adverse effects even when being heated quickly. The AC voltage is applied at a frequency which is sufficiently high that the impedance between the electrodes to which the AC voltage is applied is largely independent of the interface capacitances between those electrodes and the surface of the resistive body.

Moreover, the impedance along the arcuate locus from the point B to the point C is determined by the characteristics of the solid electrolyte per se, so that the locus is hardly affected by the resistive body surface conditions, the manner in which the electrodes are mounted on the resistive body, the kind of electrodes used, and the change thereof with elapse of time. Accordingly, when an AC voltage of the frequency higher than that for the point B of FIG. 7 is used, the impedance of the resistive body becomes smaller than the DC resistance of the resistive body, so that stable heating of the solid electrolyte at a comparatively low voltage becomes possible. To prevent localized heating, even if the frequency higher than that for the point B of FIG. 7 is used, it is preferable to select such frequencies which make the reactance due to the capacitance component $C_2$ of FIG. 6 smaller than the resistance component $R_2$.

Figure 8:
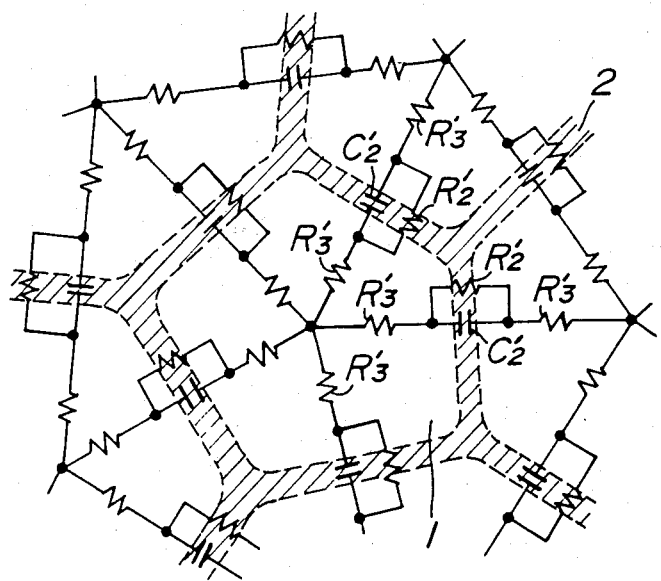
FIG. 8 is an explanatory diagram showing the relationship between the microscopic structure of the resistive body and the equivalent circuit thereof.

The resistance components $R_2$ and $R_3$ and the capacitance component $C_2$ in the electrical equivalent circuit of FIG. 6 do not represent concentrated constants but represent distributed constants as illustrated in the enlarged schematic diagram of FIG. 8. More particularly, the constants are substantially uniformly distributed in the resistive body including the fine grains 1 or thin films 5 with the NTCR and the high-resistance substance layers 2 or 6, so that even when the temperature of one distributed resistance component $R'_3$ increases due to some reasons and the resistance value thereof is reduced to allow an increase of the current therethrough, the current $i'$ therethrough is limited by the distributed capacitance component $C'_2$ in series to the distributed resistance component $R'_3$ and the voltage $V'$ applied to the capacitance component $C'_2$ and the frequency f, i.e., at $i'=2\pi f C'_2 V$. The voltage $V'$ applied across one portion of the high-resistance substance layer 2 and the distributed capacitance component $C'_2$ are both very small, so that local concentration of the electric current is prevented. Accordingly, with the present invention, the entire resistive body can be uniformly heated without any localized heating even if the resistive body is of a plate-like shape and the electrodes are mounted on the opposite surfaces of the plate-like resistive body. On the other hand, the localized heating has been experienced in the prior art, such as thermistors with negative characteristics consisting mainly of iron oxide.

Figure 9:
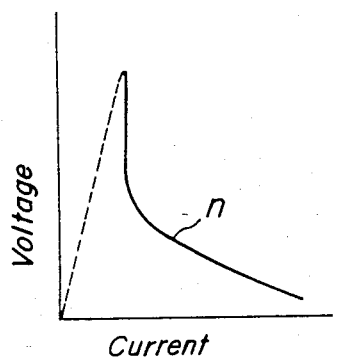
FIG. 9 is a graph showing the relationship between the voltage and the current through the resistive body.

FIG. 9 shows the relationship between the alternating current through the resistive body and the AC voltage across the resistive body, provided that the frequency of the AC voltage applied the electrodes of the resistive body is higher than that for the point B of FIG. 7. In FIG. 9, when the AC current is larger than a certain value, negative co-relation appears between the AC current and the AC voltage, namely, the voltage decreases with the increase of the current as shown by the curve n. This phenomenon is due to the temperature adjusting ability of the resistive body which ability is activated when the resistive body is heated by the alternating current as explained above by referring to FIG. 5. The negative co-relation can be advantageously used, because if the frequency and the amplitude of the alternating current for heating the resistive body are selected in the negative co-relation range of the current n of FIG. 9, the AC voltage across the resistive body is reduced in response to the flow of the alternating current depending on the temperature of the resistive body reached by the self-heating effect thereof.

In the oxygen concentration detector of FIG. 4, the temperature of the solid electrolyte 10 is accurately measured by determining the impedance of the solid electrolyte 10 from the alternating current fed into the solid electrolyte 10, which current is detected by the AC voltage detector 19 connected across the current-detecting resistor 14. This temperature measurement through the detection of the impedance will be explained now.

Figure 10:
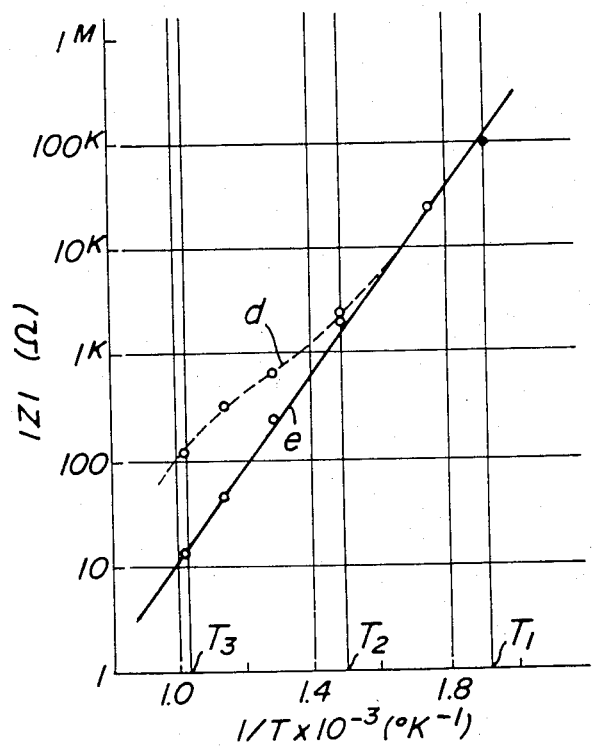
FIG. 10 is a graph showing the relationship between the temperature and the impedance of the resistive body.

The complex impedance characteristics of the resistive body varies with the temperature of the resistive body, and as the temperature increases, the impedance values at the points A, B, and C of FIG. 7 decrease and the frequencies in the proximity of the points B and C increase. FIG. 10 shows the relationship between the temperature of the resistive body and the impedance thereof for fixed frequencies. As can be seen from the figure, the temperature of the resistive body can be determined by measuring the impedance thereof. The dashed line curve d of FIG. 10 shows the result of measurement taken by using an AC voltage of that frequency which gives the impedance of the point B of FIG. 7 at the temperature $T_2$, while the solid line curve e shows the result of measurement taken by using an AC voltage of that frequency which gives the impedance of about the point C of FIG. 7 at the temperature $T_3$.

To measure the impedance, the present invention uses the AC frequency higher than that for the point B of FIG. 7, namely that frequency which causes most of the AC polarization to occur in the inside of the resistive body, as in the case of the AC frequency for heating the resistive body. The reason for using such AC frequency is in that, referring to the dashed line curve d of FIG. 10 using the frequency of the point B of FIG. 7, if the temperature increases from $T_2$ to $T_3$, the impedance varies from the point B of FIG. 7 to the point A thereof, and impedance in the region between the points A and B is considerably affected by properties of the electrodes themselves and the properties of the boundary between the electrodes and the resistive body. Besides, the impedance in this region is very unstable for the purpose of using the resistive body over a long period of time.

Figure 11:
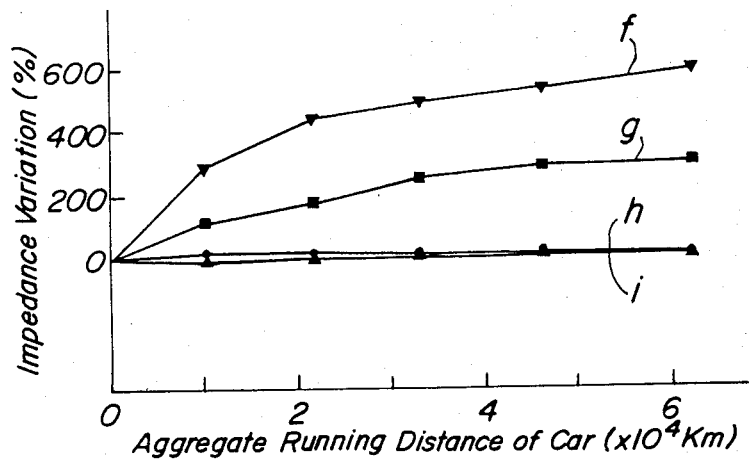
FIG. 11 is a graph showing the change of the impedance of the resistive body used in an oxygen concentration detector which is mounted on an automobile as the aggregate running distance of the automobile increase.

On the other hand, when the above-mentioned AC frequency higher than that for the point B of FIG. 7, namely that frequency which causes most of the AC polarization to occur in the inside of the resistive body, is used, the impedance is stable unless changes occur in the fine grains or the thin films or the high-resistance layers of the resistive body, so that such stability of the impedance is maintained even after a long period of use. It is more preferable to use the AC frequency in the proximity of that for the point C of FIG. 7, namely that AC frequency at which the impedance of the resistive body depends only on the fine grains or thin films. FIG. 11 clearly shows the advantages of such frequency by illustrating the variation of the impedance of the oxygen concentration detector at 400° C. with the increase of the aggregate running distance of a car carrying the oxygen concentration detector. In FIG. 11 the curve f is for DC or the frequency for the point A of FIG. 7, the cruve g is for the frequency for about the middle point of the arcuate locus between the points A and B of FIG. 7, the curve h is for the frequency for the point B of FIG. 7, and the curve i is for the frequency for the proximity of the point C of FIG. 7. The curves h and i for that frequency which causes most of the AC polarization to occur in the inside of the resistive body are highly stable even after a long period of use.

The determination of the temperature of the oxygen concentration detector by measuring the impedance thereof has advantages in the stability free from the effects of such conditions as the manner in which the electrodes are mounted. Whereby, accurate corrections, such as the temperature correction of oxygen diffusion speed in the diffusion layer 11 and the temperature correction of the resistance of the metal oxide semiconductor 9, are ensured, and the accuracy of the oxygen concentration detector is further improved.

The current-limiting resistor 13 of FIG. 4 need not be a resistor but can be replaced with a capacitor or a coil. The current-detecting resistor 14 in the circuit for the impedance detection can be also replaced with a capacitor or a coil. It should be noted that the temperature of the resistive body 10 can be kept constant by feeding back the voltage of the current-detecting resistor 14 or the like to the AC power source 12 for the heating, so as to control the voltage of the AC power source 12 or the like.

As shown in FIG. 4, the detection of the impedance is preferably effected at the heat generating resistive body 10 disposed by the metal oxide semiconductor 9, because the temperature of the metal oxide semiconductor 9 can be detected accurately and quickly thereby. One common resistor may be used both as the current-limiting resistor 13 and the current-detecting resistor 14. It is also possible to provide a separate resistive body for the impedance detection. Similarly, another separate resistive body may be provided for the control of oxygen concentration by the direct current. The position, the number, and the size of such separate resistive bodies can be selected suitably so as to meet various requirements of specific use.

The DC power source for the impedance detection may be the same as or different from the AC power source for the heating, and the frequencies of the two AC power sources may be the same as or different from each other. As to the method of mounting the electrodes, when one solid electrolyte or one resistive body is used for a plurality of functions, electrodes for different functions, such as the electrodes for the heating and the electrodes for applying the direct current, may be separated and mounted independently.

When a solid electrolyte is used as the resistive body for causing the self-heating, the self-heating start temperature Ts of FIG. 5 is high and the self-heating is hard to start. In this case, an auxiliary heater (not shown) may be provided in or by the resistive body or in or by the metal oxide semiconductor, so as to heat the resistive body until the self-heating start temperature Ts is reached.

If it is not necessary to apply a direct current to the resistive body for controlling the oxygen concentration therein, the self-heating start temperature Ts should be reduced by using such materials as zinc oxide (ZnO) or titania (TiO$_2$) which are not solid electrolyte. The value of the self-heating start temperature Ts is determined mainly by the resistive value of the resistive body and the voltage applied thereto. The power supply to the auxiliary heater should be interrupted once the self-heating of the resistive body is started.

The shape of the resistive body or the metal oxide semiconductor to be used in the oxygen concentration detector of the present invention can be plate-like, cylinder-like, cylinder-like with a bottom, or thin-film-like. When the metal oxide semiconductor is in the form of thin film, the resistance value of the metal oxide semiconductor can be made variable in response to the change of oxygen concentration without making it porous as shown in FIG. 4. The solid electrolyte or the resistive body capable of self-heating may be provided with a portion which is thinner than the remaining portions thereof, so that such thin portion may be made hottest therein, and is such thin portion is disposed adjacent to the position with which the exhaust gas is easily brought into contact, the sensitivity and the response of the oxygen concentration detector are both improved. If the diffusion layer is uniformly provided only at the portion adjacent to the heated portion, the steep change of the resistance value is ensured in the oxygen concentration detector. More particularly, in conventional oxygen concentration detectors, if the thickness of the diffusion layer is uneven, the diffusion speed of oxygen therethrough becomes uneven, so that a difference is produced between the air-fuel ratio λ for causing the sudden change in the resistance value of the thick portion and the air-fuel ratio λ for causing the sudden change in the resistance value at the thin portion, whereby the steepness of the overall sudden change of the resistance value is lost. On the other hand, if the heating is caused at a certain localized portion, only such localized portion acts as the essential oxygen concentration detector, so that it is sufficient to keep the thickness uniformity of the diffusion layer at such localized portion. Preferably, the diffusion layer for the non-heated portion is made thicker than that for the heated localized portion, or the non-heated part of the electrode is coated with an airtight layer. Even if the heated portion is localized, the present invention determines the temperature of the resistive body by detecting the impedance thereof, so that the temperature of the heated portion can be accurately measured.

The invention will be described in further detail by referring to an example.

EXAMPLE 1

Figure 12:
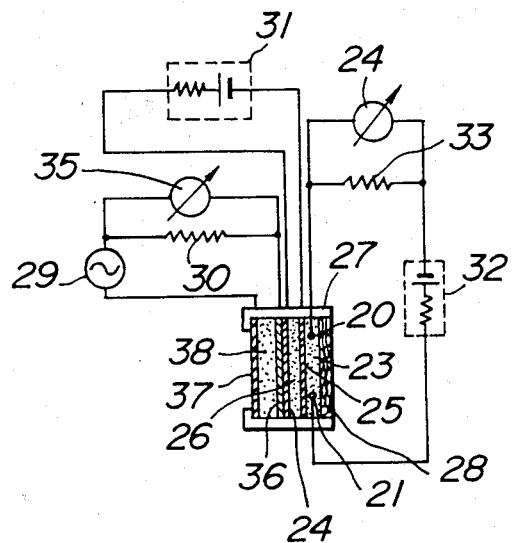
FIG. 12 is an explanatory diagram of an oxygen concentration detector which was tested as an example of the present invention.

Referring to FIG. 12, a porous disk-shaped titania (TiO$_2$) porcelain 23 with an outer diameter of 7 mm and a thickness of 1.2 mm was prepared while embedding electrodes 20 and 21 therein. A disk-shaped zirconia (ZrO$_2$) solid electrolyte 26 with an outer diameter of 7 mm and a thickness of 1.2 mm and having electrodes 24 and 25 was mounted on one side surface of the disk-shaped titania porcelain 23, and a disk-shaped zinc oxide (ZnO) resistive body 38 with an outer diameter of 7 mm and a thickness of 1.5 mm and having electrodes 36 and 37 was mounted on the solid electrolyte 26, and the thus assembled disk-shaped members were placed in an alumina (Al$_2$O$_3$) porcelain case 27. A diffusion layer 28 made of porous alumina spinel is mounted on the opposite side surface of the titania porcelain 23. Whereby, an oxygen concentration detector was prepared.

An AC power source 29 and 30 kHz output voltage of 30 V with sinusoidal waveform was connected across the resistive body 38 through a current-limiting resistor 30. A DC power source 31 was connected across the solid electrolyte 26, so as to cause movement of oxygen from the electrode 25 of the solid electrolyte 26 to the other electrode 24 thereof. Another DC power source 32 of 12 V was connected across the titania porcelain 23 through a current-detecting resistance 33 of 2 kΩ, and a DC voltage detector 34 was connected across the current-detecting resistor 33 to monitor the voltage thereacross.

The oxygen concentration detector thus produced was placed in an engine exhaust gas system with known levels of air-gas ratio λ. The response of the voltage (V) of the oxygen concentration detector was measured at the DC voltage detector 34 by gradually changing the air-fuel ratio λ at the exhaust gas temperature of 250° C., 600° C., and 900° C. For reference, measurements were also taken without heating, as an example of the prior art. In this measurement, no direct current was applied to the solid electrolyte 26. The result of the example of the invention is shown in FIG. 13, while that of the prior art is shown in FIG. 14.

As can be seen from FIG. 13 and FIG. 14, in the case of the present invention, the output voltage was substantially unchanged even when the exhaust gas temperature varied, while in the case of the prior art, the output voltage changed greatly upon variation of the exhaust gas temperature under the conditions of the air-fuel ratio λ being less than unity (<1). During the measurement, the impedance of the resistive body 38 was measured by checking the voltage across the current-limiting resistor. At the same time, the power applied to the resistive body 38 was also measured. The result is shown in Table 1.

TABLE 1

| Exhaust gas temperature (°C.) | Impedance of resistive body (Ω) | Temperature determined by impedance (°C.) | Power applied to resistive body (W) |
|---|---|---|---|
| 250 | 40 | 730 | 3.9 |
| 600 | 13 | 810 | 1.8 |
| 900 | 2.7 | 920 | 0.3 |

As can be seen from Table 1, the power applied to the resistive body was reduced as the exhaust gas temperature increased. The temperature change as determined by the impedance was suppressed to about one third of the variation of the exhaust gas temperature.

Thereafter, the relationship between the air-fuel ratio λ and the output voltage was measured by the same method as before, under the conditions of the exhaust gas temperature of 250° C. and the direct current through the solid electrolyte at 1 mA, 2 mA, 3 mA, and 4 mA. The result is shown in FIG. 15.

As can be seen from FIG. 15, the steepness of the output voltage change was not lost even if the direct current was applied, and that air-fuel ratio λ at which the output voltage varied suddenly could be controlled by regulating the direct current. In FIG. 15, the curve j shows the air-fuel ratio λ vs. output voltage relationship for the direct current of 1 mA, the curve k shows the same relationship for the direct current of 2 mA, the curve 1 shows the same relationship for the direct current of 3 mA, and the curve m shows the same relationship for the direct current of 4 mA. In the case of the prior art without the heating, the voltage of the DC power source increased to more than 150 V and the desired direct current could not be applied, and that air-fuel ratio λ at which the voltage across the current-detecting resistor 33 varied suddenly could not be measured.

EXAMPLE 2

Figure 16:
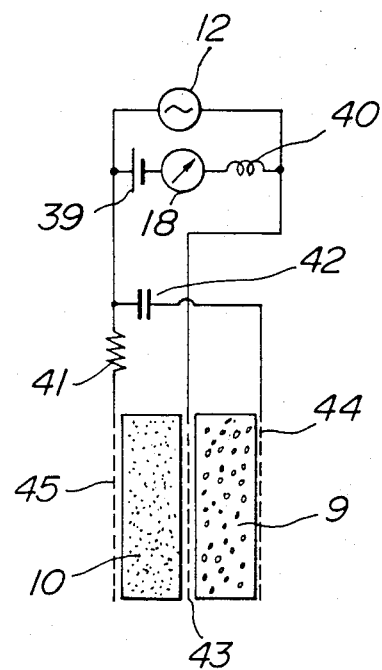
FIG. 16 is a diagrammatic illustration of another embodiment of the oxygen concentration detector according to the present invention.

FIG. 16 shows a schematic diagram of another embodiment of the invention, in which electrode 43 is disposed between semiconductor 9 such as TiO$_2$ and SnO and the resistive bodies 10 such as solid electrolytes. An electrode 44 is mounted on that surface of the resistive body 10 which is opposite to the electrode 43, and a capacitor 42 in series with an AC current-limiting resistor 41 is connected across the electrode 45 mounted on the semiconductor 9 and the thus mounted electrode 44. In this embodiment, self-heating is caused in the resistive body 10 but not in the semiconductor 9, provided that the capacitive reactance of the capacitor 42 is sufficiently small, so that the electrode 45 is difficult to peel off. The Ac current-limiting resistor 41 may be replaced with an inductor. The resistive body 10 is not necessarily required to be an oxygen-ion-conducting solid electrolyte, and only requirement therefor is to have a negative temperature coefficient of electric resistance.

In this embodiment, AC power source is connected to one couple of electrodes 43, 44 and the other couple of electrodes 43, 45. AC current is only applied to between said electrodes 43 and 44, since resistor 41 has a high resistance value so as to hardly flow AC current through resistor 41. DC current of DC power source 39 is cut in capacitor 42 so that DC current is only applied to between electrodes 43 and 45. AC power source 21 cause to self-heat the resistive body 10 and DC meter 18 can only detect resistance of semiconductor 9 separate from resistive body 10.

The inductor 40 can be operable so as not to flow AC current through DC meter 18. The resistance of semiconductor 9 can be measured by DC meter 18 correctly with the aid of inductor 40, so that the circuit arrangement can be simplified and the lead wire can be eliminated to one side circuit by earthing the other side circuit.

As described in the foregoing, in the oxygen concentration detector according to the present invention, a resistive body is heated by applying an AC voltage thereto, and a metal oxide semiconductor is heated by the self-heating of the resistive body, so that the risk of the breakage of heater wires experienced in the prior art is eliminated. The oxygen concentration detector of the present invention is small in size and simple in construction, and has the temperature self-control properties so as to ensure easy heating of only the necessary portion with a small power. The heating in the oxygen concentration detector can be applied in a stable fashion with a comparatively low voltage over a long period of time, so as to ensure high accuracy and quick response of the measurement even when the temperature of the gas being measured is low. That value of the air-fuel ratio λ at which the resistance value of the metal oxide semiconductor varies suddenly can be easily and accurately controlled by applying a direct current to a solid electrolyte forming the resistive body. In the present invention, local heating of the solid electrolyte can be advantageously used, so as to facilitate the formation of uniformity in the thickness of the heated portion of the diffusion layer, whereby of the resistance value of the metal oxide semiconductor is ensured. Furthermore, the temperature change of the diffusion layer is small, so that the variation of the diffusion speed is kept low, and the variation of that air-fuel ratio λ at which the resistance values varies suddenly is small. With present invention, the application of the direct current to the resistive body does not cause chipping of the electrode, and the temperature of the oxygen concentration detector can be easily measured by checking the impedance in a stable fashion over a long period of time.

Thus, the oxygen concentration detector of the present invention has excellent performance in terms of the accuracy, the response, and the durability. Furthermore, the structure of the oxygen concentration detector of the invention is very simple. In short, the present invention provides an oxygen concentration detector which has the above-mentioned advantages and which is particularly suitable for detection of the oxygen concentration in the exhaust gas from internal combustion engines, so that the invention contributes greatly to the industry.

Although the invention has been described with a certain degree of particularly, it is understood that the present disclosure has been made only by way of example and that numerous changes in details of construction and the combination and arrangement of parts may be resorted to without departing from the scope of the invention as hereinafter claimed.

What is claimed is:

1. An oxygen concentration detector for detecting oxygen concentration in gases, comprising:
   a semiconductor body whose electric resistance varies with oxygen partial pressure of an ambient atmosphere thereof, said semiconductor body being located between at least two separate electrode and said electrodes being in contact with said semiconductor body;
   a resistive body having a composition including a number of portions with a negative temperature coefficient of electric resistance and high-resistance substance layers separating said portions one from the other, at least two separate electrodes contacting said resistive body and having the resistive body located therebetween;
   an AC power source connected to said at least two separate electrodes contacting said resistive body, said AC power source applying an AC current to said resistive body so as to heat the resistive body, said AC power source being arranged to supply an AC voltage at a frequency sufficiently high that an impedance between said at least two electrodes to which AC voltage is applied is largely independent of interface capacitances between said electrodes to which AC voltage is applied and a surface of said resistive body, said resistive body being so related to said semiconductor that said semiconductor is heated by said resistive body upon application of said AC current; and
   means for measuring a resistance of the semiconductor body with variances of the oxygen partial pressure.

2. An oxygen concentration detector for detecting oxygen concentration in gases, comprising:
   a semiconductor body whose electric resistance varies with oxygen partial pressure of an ambient atmosphere thereof said semiconductor body being located between at least two separate electrodes and said electrodes being in contact with said semiconductor body;
   a resistive body having a composition including a number of portions with a negative temperature coefficient of electric resistance and high-resistance substance layers separating said portions one from the other, at least two separate electrodes contacting said resistive body and having the resistive body located therebetween;
   an oxygen ion conductive solid electrolyte body located between at least two separate electrodes and said electrodes being in contact with said oxygen ion conducting solid electrolyte body, thereby forming an oxygen pump;
   an AC power source connected to said at least two separate electrodes contacting said resistive body, said AC power source applying an AC current to said resistive body so as to heat the selected resistive body, said AC power source being arranged to supply an AC voltage at a frequency sufficiently high that an impedance between said at least two electrodes to which AC voltage is applied is largely independent of interface capacitances between said electrodes to which AC voltage is applied and a surface of said resistive body, said resistive body being so related to a semiconductor that said semiconductor is heated by said resistive body upon application of said AC current;
   a DC source connected to said separate electrodes contacting said oxygen pump for controlling oxygen partial pressure around the semiconductor by applying DC current through said electrolyte body; and
   means for measuring a resistance of the semiconductor body with variances of the oxygen partial pressure.

3. The detector of claim 1 or 2, wherein said portions of said resistive body with a negative temperature coefficient of electric resistance are fine grains.

4. The detector of claim 1 or 2, wherein said portions of said resistive body with a negative temperature coefficient of electric resistance are thin films.

5. The detector of claim 1 or 2, wherein an AC current and an AC voltage applied between the electrodes have a negative relation, such that when one increases, the other decreases.

6. The detector of claim 1 or 2, wherein the AC current has a frequency at which an impedance of electrostatic capacitance at highly resistant region layers interposed between fine grains or thin films is smaller than a resistance at the highly resistant region layers.

7. The detector of claim 1 or 2, further comprising means for detecting the impedance of one of said bodies by applying an AC current therethrough, said AC current having a frequency sufficiently high such that an impedance between said at least two electrodes to which AC voltage is applied is largely independent of interface capacitances between said electrodes to which AC voltage is applied and a surface of said resistive body.

8. The detector of claim 1 or 2, further comprising an auxiliary heating means related to one of said bodies.

9. The detector of claim 1 or 2, wherein at least one electrode of said semiconductor body is connected to at least one electrode of said resistive body through a capacitor, said resistive body being heated by said AC current.

10. The detector of claim 2, wherein said resistive body and said oxygen ion conductive solid electrolyte body comprise a unitary body.

* * * * *